United States Patent [19]

Kataoka et al.

[11] 4,150,117

[45] Apr. 17, 1979

[54] PROCESS FOR THE PREPARATION OF GASTROINTESTINAL HORMONE

[75] Inventors: Tsunehiko Kataoka, Kakamigahara; Sinzou Watanabe, Kounan; Syouji Kitakaji, Kakamigahara; Koichi Ogawa, Inazawa; Seiji Yoshida, Kakamigahara, all of Japan

[73] Assignee: Eisai Co., Ltd., Tokyo, Japan

[21] Appl. No.: 875,556

[22] Filed: Feb. 6, 1978

[30] Foreign Application Priority Data

Feb. 10, 1977 [JP] Japan .................................. 52-12974

[51] Int. Cl.² ............................................. A61K 35/38
[52] U.S. Cl. .................................................... 424/104
[58] Field of Search ......................................... 424/104

[56] References Cited

U.S. PATENT DOCUMENTS

| | | | |
|---|---|---|---|
| 2,099,708 | 11/1937 | Sharp et al. | 424/104 |
| 3,013,944 | 12/1961 | Jorpes et al. | 424/104 |

Primary Examiner—Sam Rosen
Attorney, Agent, or Firm—Blanchard, Flynn, Thiel, Boutell & Tanis

[57] ABSTRACT

Gastrointestinal hormone is prepared by heating the small intestine of mammal in an aqueous solution of a salt and extracting the gastrointestinal hormone and purifying it.

7 Claims, No Drawings

PROCESS FOR THE PREPARATION OF GASTROINTESTINAL HORMONE

BACKGROUND OF THE INVENTION

1. Field of the Invention

The present invention relates to a process for preparing a gastrointestinal hormone from small intestine of a mammal at a high yield.

2. Description of Prior Arts

As the process for the preparation of gastrointestinal hormone, there has been a well known process in which the hormone is directly extracted from the small intestine with ethanol, dilute hydrochloric acid or the like. According to this process, however, the efficiency of the extraction of gastrointestinal hormone is extremely low, and this process cannot be used as an industrial process.

As improvements of this process, there have been proposed a process which comprises mincing the small intestine and extracting gastrointestinal hormone with hot dilute acetic acid (Japanese Pat. No. 535,068) and a process which comprises heating the small intestine in boiling water, mincing the heated small intestine and extracting gastrointestinal hormone at room temperature with dilute acetic acid (U.S. Pat. No. 3,013,944). These processes are still insufficient to use them in the mass-production of gastrointestinal hormone. In the former process, the yield of the hormone is low, because they are decomposed and inactivated at the mincing and subsequent steps by various proteases contained in the small intestine. In the latter process, since the small intestine is heated in boiling water, the protease are inactivated, but since the gastrointestinal hormone is easily soluble in water, the loss of the hormone in boiling water is extreme. For example, when the small intestine is heated in boiling water for 5 to 10 minutes, about 30 to about 40% of total secretin and about 20 to about 30% of total cholecystokinin-pancreozymin are lost in boiling water. Therefore, in both conventional methods, a considerable quantity of gastrointestinal hormone is lost in the initial stage of the preparation process.

SUMMARY OF THE INVENTION

It is therefore a primary object of the present invention to provide an improvement of the process for treating the small intestine in which gastrointestinal hormone can be prepared at a high yield.

In accordance with the present invention, there is provided a process for the preparation of gastrointestinal hormone characterized by heating the small intestine of a mammal in an aqueous solution of a salt, extracting gastrointestinal hormone and purifying it.

The upper portion of the small intestine, inclusive of the duodenum, of pig or cattle is preferably used, because it is easily available and the hormone content is high therein.

As the salt to be used for an extracting aqueous solution, there may be used inorganic and organic acid salts of alkali and alkaline earth metals.

For example, there can be used sodium chloride, potassium chloride, calcium acetate, calcium chloride and magnesium acetate, and the use of sodium chloride is especially preferred. A preferred concentration is about 0.5 to about 5.0% by weight.

Heating of the small intestine is carried out under such conditions that enzymes contained in the small intestine are inactivated. If the heating temperature is about 90 to about 100° C., sufficient results are obtained when the heating is continued for 5 to 10 minutes.

After the small intestine is treated with a hot, aqueous solution containing a salt, it can be used immediately as a starting material for the extraction of gastrointestinal hormones and if necessary, it can be stored in a refrigerator without substantial lowering of the hormone content.

In the further purification of gastrointestinal hormones, there may be employed conventional methods. Each gastrointestinal hormone can be extracted and purified by an appropriate combination of the following methods. The hormone is extracted with ethanol, methanol, isopropanol, dilute hydrochloric acid or dilute acetic acid solution and then adsorbed onto a resin such as carboxymethyl cellulose, triethylaminoethylcellulose and QAE-Sephadex. The hormone is effectively purified by a fractionation method using an organic solvent such as acetone or by the gel filtration method. The recovery of these hormones from the solvent used is performed by the salting-out method using sodium chloride or ammonium sulfate.

According to the process of the present invention decomposition of gastrointestinal hormone by enzymes can be prevented and the loss of gastrointestinal hormone in an aqueous solution of sodium chloride is much smaller than the loss of the hormone in water. As a result, it is possible to prepare alimentary canal hormone at a high yield.

The present invention will now be described in detail by reference to the following Examples.

EXAMPLE 1

To 40 l of a boiling aqueous solution containing 0.9% of sodium chloride was added 10 Kg of the upper portion (along 2 m below the pylorus) of the fresh small intestine as quickly as possible after about 100 pigs were slaughtered and the small intestine was boiled for 5 minutes. The boiled small intestine was collected by a metal wire basket, and it was sufficiently washed by pouring hot water thereto to remove fat. The resulting boiled small intestine was minced and put into 40 l of 0.1 N acetic acid previously heated at 90° to 95° C. Agitation was conducted at the same temperature for 10 minutes to effect complete extraction of gastrointestinal hormone. Then, the mixture was naturally cooled to room temperature and allowed to stand still overnight at 4° C. Then, 400 g of Celite was added to the mixture and the solids were separated by filtration using filter paper. The solids were washed with 3 l of 0.1 N acetic acid and combined with the filtrate. To the resulting slightly yellowish orange transparent solution was added 1.2 Kg (dry weight=400 g) of carboxymethyl cellulose which was previously activated, and the mixture was agitated for 30 minutes at room temperature and allowed to stand still at 4° C. overnight. The carboxymethyl cellulose was separated by filtration, washed with 3 l of cold water, suspended in 5 l of 0.1 N hydrochloric acid and agitated at room temperature for 30 minutes to elute the adsorbed substances from the carboxymethyl cellulose. The carboxymethyl cellulose was recovered by suction filtration and washed with 1 l of 0.1 N hydrochloric acid. The washing liquid was combined with the filtrate, and 0.1 Kg of sodium chloride was added to the solution. Then, the mixture was agitated at room temperature for 2 hours and allowed to stand still at 4° C. overnight. The precipitate, which was recovered by filtration, again dissolved in 2 l of distilled water and the insoluble substances were removed by filtration. Then, 600 g of sodium chloride was dissolved in the filtrate and the solution was allowed to stand still at 4° C. overnight. The precipitate was recovered by filtration and the recovered faintly yellowish cake was dissolved in water and lyophylized. The biological activities (Crick, Harper and Raper unit) and (Ivy Dog unit) of the crude gastrointestinal hormones, namely secretin and cholecystokinin-pancreozymin, were determined according to the methods disclosed in J. Physiol., 110, p. 396, 1950 and J. Physiol., 95, p. 35, 1930, respectively.

In the foregoing experiment, the small intestine was heated for 5 minutes in a 0.9% aqueous solution of sodium chloride. In order to clarify the extracting condition, gastrointestinal hormones were prepared by the manner similar to the foregoing experiment, except for changing the kind of the salt, concentration of the salt and time of heating.

For comparison, the small intestine was heated in boiling water and subsequent steps were conducted in the same manner as described above (Control 1). Further, the small intestine was directly minced and extracted with the hot acetic acid and then subsequent steps were conducted in the same manner as described above (Control 2).

Obtained results are shown in Table 1.

Table 1

| Extracting condition of small intestine | | Yield (g) of Alimentary Canal Hormone | Activity of Secretin | | Activity of Cholecystokinin-Pancreozymin | |
|---|---|---|---|---|---|---|
| Kind of Aqueous Solution | Boiling Time (minutes) | | Specific Activity (unit/mg) | Total Activity (unit) | Specific Activity (unit/mg) | Total Activity (unit) |
| Process of Present Invention | | | | | | |
| 0.9% sodium chloride | 5 | 32.2 | 2.2 | $7.1 \times 10^4$ | 0.7 | $2.3 \times 10^4$ |
| 1.8% sodium chloride | 5 | 35.0 | 2.0 | $7.0 \times 10^4$ | 0.5 | $1.8 \times 10^4$ |
| 0.9% sodium chloride | 10 | 36.0 | 2.0 | $7.1 \times 10^4$ | — | — |
| 1.15% potassium chloride | 10 | 19.3 | 3.0 | $5.8 \times 10^4$ | — | — |
| 0.8% calcium acetate | 5 | 24.9 | 2.5 | $6.2 \times 10^4$ | 1.0 | $2.5 \times 10^4$ |
| 0.7% magnesium acetate | 5 | 24.7 | 2.7 | $6.7 \times 10^4$ | — | — |
| Control 1 | | | | | | |
| boiling water | 5 | 26.7 | 1.5 | $4.0 \times 10^4$ | 0.5 | $1.3 \times 10^4$ |
| boiling water | 10 | 34.6 | 1.3 | $4.5 \times 10^4$ | — | — |
| Control 2 | | | | | | |
| — | — | 22.5 | 1.5 | $3.4 \times 10^4$ | 0.6 | $1.4 \times 10^4$ |

As will be apparent from the results shown in Table 1, according to the process of the present invention, the activity yields of secretin and cholecystokinin-pancreozymin are much improved over those in Controls, and the specific activity of secretin is very high.

EXAMPLE 2

To 40 l of a boiling aqueous solution containing 0.9% of sodium chloride was added 10 Kg of the upper portion (along 2 meters below the pylorus) of the fresh small intestine as quickly as possible after about 100 pigs were slaughtered and the small intestine was boiled for 5 minutes. The boiled small intestine was collected by a metal wire basket, and it was sufficiently washed by pouring hot water thereto to remove fat. The resulting boiled small intestine was minced and put into 40 l of 0.1 N acetic acid previously heated at 90° to 95° C. Agitation was conducted at the same temperature for 10 minutes to effect complete extraction of gastrointestinal hormone. Then, the mixture was naturally cooled to room temperature and allowed to stand still overnight at 4° C. Then, 400 g of Celite was added to the mixture and the solids were separated by filtration using filter paper. The solids were washed with 3 l of 0.1 N acetic acid and combined with the filtrate. To the resulting slightly yellowish orange transparent solution was added 1.2 Kg (dry weight=400 g) of previously activated carboxymethyl cellulose, and the mixture was agitated for 30 minutes at room temperature and allowed to stand still at 4° C. overnight. The carboxymethyl cellulose was separated by filtration, washed with 3 l of cold water, suspended in 5 l of 0.1 N hydrochloric acid and agitated at room temperature for 30 minutes to elute the adsorbed substance from the carboxymethyl cellulose. The carboxymethyl cellulose was recovered by suction filtration and washed with 1 l of 0.1 N hydrochloric acid. The washing liquid was combined with the filtrate, and 0.8 Kg of sodium chloride was added to the mixture. Then, the mixture was agitated at room temperature for 2 hours and allowed to stand still at 4° C. overnight. The precipitate was recovered by filtration and dissolved in 2 l of distilled water, and the insoluble substance was removed by filtration. Then, 600 g of sodium chloride was dissolved in the filtrate and the solution was allowed to stand still at 4° C. overnight. The precipitate was recovered by filtration and the recovered slightly yelllowish cake was dissolved in 130 ml of distilled water, and the pH was adjusted to 3.0 by 1 N sodium hydroxide. Then, 2 l of isopropanol was added to the solution, and the mixture was agitated at 30 to 35° C. for 2 hours to extract secretin. Then, 20 g of Celite was added the insoluble substance was recovered by suction filtration. The insoluble substance was suspended in 2 l of methanol and the suspension was agitated at room temperature for 2 hours to effect complete extraction. The methanol was subjected to suction filtration to remove the insoluble solids and the filtrate was combined with the isopropanol layer. The mixture was evaporated under a reduced pressure at a bath temperature of 50° C. The residue was dissolved in 300 ml of distilled water and the pH was adjusted to 7.0 by 1 N sodium hydroxide, and the precipitated insoluble substance was removed by filtration using filter paper and the pH of the filtrate was adjusted to 3.0 by 2 N hydrochloric acid. Then, 100 g of sodium chloride was added to the total amount of 330 ml of the solution to salt-out. The solution was allowed to stand still at 4° C. overnight, and the precipitate was collected by suction filtration, dissolved in 50 ml of distilled water and lyophylized. The biological activity of the so obtained secretin was determined according to the method described in Example 1.

In the foregoing experiment, the small intestine was heated for 10 minutes in a 0.9% aqueous solution of sodium chloride. Similarly, gastrointestinal hormones were prepared while changing the kind of the salt, a concentration of the salt and the heating time.

On the other hand, the small intestine was heated in boiling water and subsequent steps were conducted in the same manner as described above (Control 1). Further, the small intestine was directly minced and extracted by the hot acetic acid and subsequent steps were conducted in the same manner as described above (Control 2).

Obtained results are shown in Table 2.

Table 2

| Extracting conditions of small intestine | | Secretin | | |
|---|---|---|---|---|
| Kind of Aqueous Solution | Boiling Time (minutes) | Yield (g) | Specific Activity (unit/mg) | Total Activity (units) |
| Process of Present Invention | | | | |
| 0.9% sodium chloride | 5 | 2.072 | 19.3 | $4.0 \times 10^4$ |
| 0.9 % sodium chloride | 5 | 2.182 | 20.3 | $4.4 \times 10^4$ |
| 1.8% sodium chloride | 5 | 2.367 | 16.0 | $3.7 \times 10^4$ |
| 1.15% sodium chloride | 5 | 1.625 | 20.0 | $3.3 \times 10^4$ |
| 0.7% magnesium acetate | 5 | 1.821 | 20.0 | $3.6 \times 10^4$ |
| Control 1 | | | | |
| boiling water | 5 | 2.050 | 13.0 | $2.7 \times 10^4$ |
| Control 2 | | | | |
| — | — | 2.039 | 7.7 | $1.6 \times 10^4$ |

As will be apparent from the results shown in Table 2, according to the process of the present invention, the total activity of secretin is much improved over those in Controls, and the specific activity of secretin is very high.

The embodiments of the invention in which an exclusive property or privilege is claimed are defined as follows:

1. A process for obtaining gastrointestinal hormone, which comprises the steps of heating mammalian small intestine in an aqueous solution of a salt selected from the group consisting of alkali metal salts and alkaline earth metal salts of inorganic acids and organic acids, at a temperature and for a time effective to inactivate the enzymes contained in said small intestine; then extracting the gastrointestinal hormone from the treated small intestine and purifying the gastrointestinal hormone.

2. A process according to claim 1 in which the heating step is performed at a temperature of about 90° to about 100° C. for a period of about 5 to about 10 minutes, and the concentration of said salt in said aqueous solution is from about 0.5 to about 5.0% by weight.

3. A process according to claim 1 in which the extracting step is performed by contacting the treated small intestine with an extracting agent selected from the group consisting of ethanol, methanol, isopropanol, dilute hydrochloric acid and dilute acetic acid to obtain an extract containing the gastrointestinal hormone, treating the extract to absorb the gastrointestinal hormone on a resin and then recovering the gastrointestinal hormone from the resin.

4. A process as claimed in claim 1, wherein said salt is selected from the group consisting of sodium chloride, potassium chloride, calcium acetate, calcium chloride and magnesium acetate.

5. A process as claimed in claim 1 or claim 2, wherein said salt is sodium chloride.

6. A process as claimed in claim 1, wherein said mammalian small intestine is obtained from pigs.

7. A process as claimed in claim 1, wherein said mammalian small intestine is obtained from cattle.

* * * * *